United States Patent [19]

Labaune et al.

[11] Patent Number: 4,709,051
[45] Date of Patent: Nov. 24, 1987

[54] NOVEL AROYLPYRROLES, THEIR PRODUCTION AND THEIR USE IN IMMUNOLOGIC THERAPY

[75] Inventors: Jean-Pierre Labaune, Moulignon-Ponthierry; Pierre B Essin, Chilly-Mazarin, both of France

[73] Assignee: Albert Rolland, S.A., Paris, France

[21] Appl. No.: 842,899

[22] Filed: Mar. 24, 1986

[51] Int. Cl.[4] ......................................... C07C 207/323
[52] U.S. Cl. .................................................. 548/533
[58] Field of Search ......................... 548/533; 514/423

[56]     References Cited
    U.S. PATENT DOCUMENTS
    4,194,003  3/1980  LaForest et al. .................... 514/423
    FOREIGN PATENT DOCUMENTS
    2405246  10/1978  France .

Primary Examiner—Joseph Paul Brust
Attorney, Agent, or Firm—Omri M. Behr

[57] ABSTRACT

This invention relates to novel aroylated derivatives of pyrrole. More particularly it provides the novel naphthoyl derivatives of pyrrolyl-2-carboxylic acid having the general formula I:

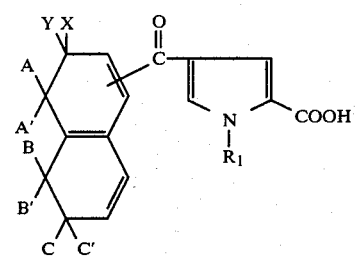

wherein:
$R_1$ is a lower alkyl radical, a phenyl radical or a hydrogen;
X is a hydrogen, a hydroxy or a methylsulphinyl group;
Y is a hydrogen or together with A' a double bond;
A is a hydrogen or a hydroxy;
A' is a hydrogen or together with Y a double bond;
B is a hydrogen or a hydroxy;
B' is a hydrogen or together with C a double bond;
C is a hydrogen or together with B' a double bond;
C' is a hydrogen, a hydroxy or a methylsulphinyl group;
  with the proviso that X, Y, A, A', B, B', C and C' are not simultaneously a hydrogen.

The compounds according to this invention, may exist in the free acid form or as a salt.

They found a use in human or veterinary medicine in the form of pharmaceutical compositions for preventing or treating the immunological diseases.

7 Claims, 11 Drawing Figures

MASS SPECTRA OF:

N-methyl-4-(naphthoyl-1)-
pyrrolyl-2-carboxylic acid

N-(naphthoyl-1)-pyrrolyl-2-
carboxylic acid as synthesised 4-(naphthoyl-1)-pyrrolyl-2-
carboxylic acid obtained by
biological extraction

MASS SPECTRA

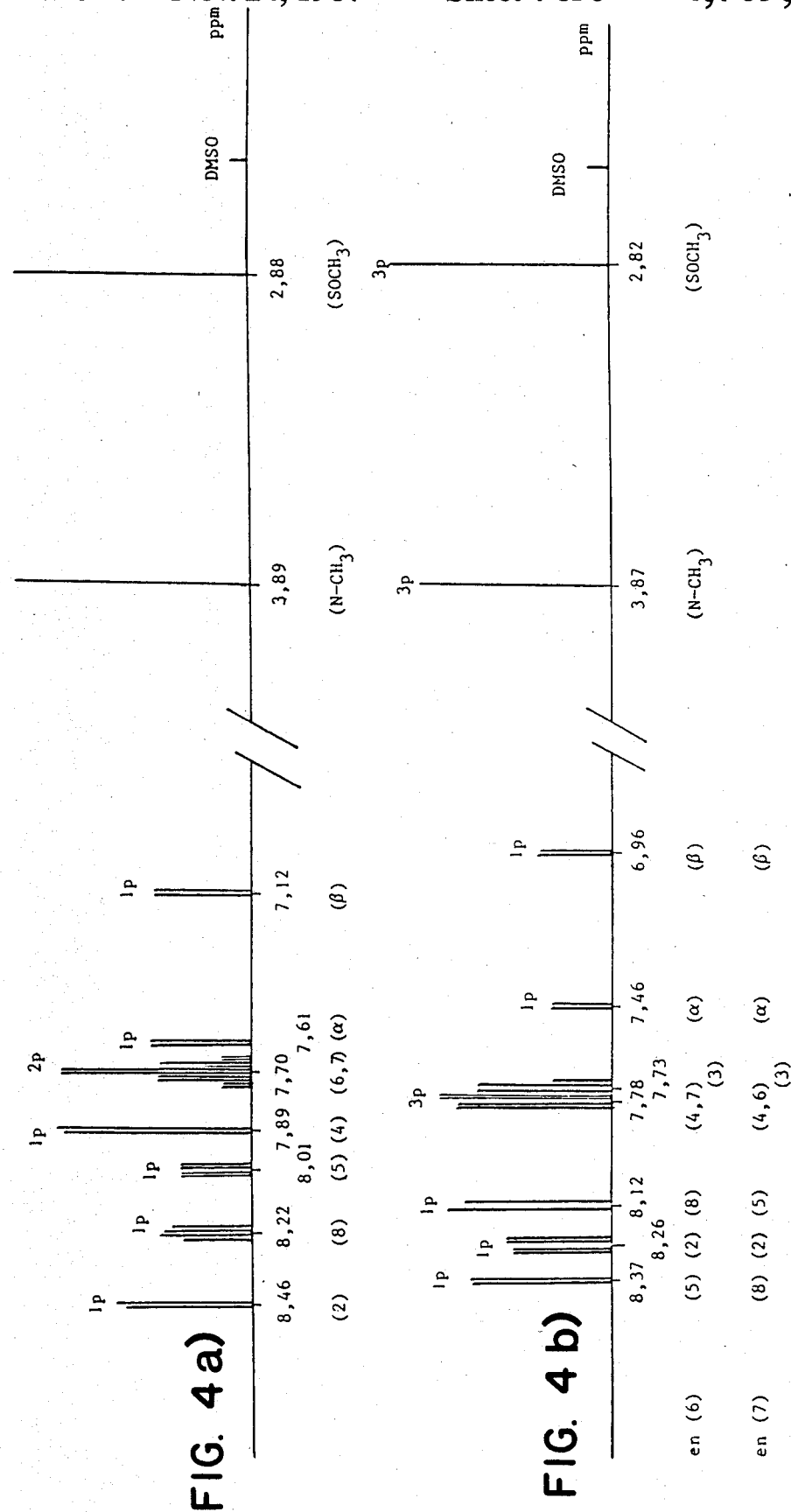

COUPLING SHOWN AFTER SUCCESSIVE IRRADIATIONS AT (8.46), (8.22), (8.01) ppm AND INTERPRETATION OF THE AROMATIC MOIETY OF THE NMR SPECTRUM OF THE (3-METHYLSULPHINYLNAPHTHOYL-1) DERIVATIVE RECOVERED BY HPLC COUPLING SHOWN AFTER SUCCESSIVE IRRADIATIONS AT (8.46), (8.22), AND (8.01) ppm AND SIGNIFICATION OF THE AROMATIC MOIETY OF THE RMN SPECTRUM OF N-METHYL-4-(6-METHYLSULPHINYLNAPHTHOYL-1)-PYRROLYL-2-CARBOXYLIC ACID

NOVEL AROYLPYRROLES, THEIR PRODUCTION AND THEIR USE IN IMMUNOLOGIC THERAPY

PRIOR ART

The prior Art may best illustrated by the following references:
French Pat. No. 2.405.246
U.S. patent application Ser. No. 738,043, now U.S. Pat. No. 4,617,315.

PREFERRED EMBODIMENTS

This invention relates to novel aroylated derivatives of pyrrole. More particularly it relates to 4-aroylpyrrolyl-2-carboxylic acid.

This invention specifically provides novel naphthoyl derivatives of pyrrolyl-carboxylic acid having the general formula (I):

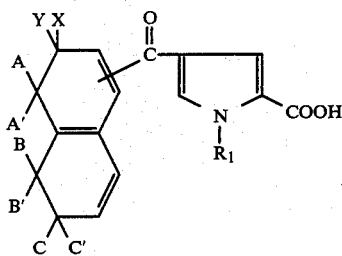

wherein:
$R_1$ is a lower alkyl radical, a phenyl or a hydrogen;
X is hydrogen, a hydroxy or a methylsulphinyl group;
Y is a hydrogen or with A' is a double bond;
A is hydrogen or hydroxy;
A' is hydrogen or together with Y is a double bond;
B is hydrogen or hydroxy;
B' is hydrogen or with C is a double bond;
C is hydrogen or with B' is a double bond;
C' is hydrogen, hydroxy or a methylsulphinyl group ($CH_3SO$); with the proviso that X, Y, A, A', B, B', C and C' are not simultaneously a hydrogen.

These compounds may be in the form of a free acid or in the form of an addition salt thereof as for example an alkali metal salt, an earth alkaline metal salt, an iron salt, an aluminum salt, a magnesium salt, an organic base addition salts as for example an alkylamine salt, a dialkylamine salt, an arylalkylamine salt, a tri-lower-alkylamine, a cyclanylamine, a basic amino-acid salt, an amino-alkanol salt, a cyclic base salt such as dihydropyridine, lutidine or collidine salt.

The compounds of general formula I in which X is a hydroxy or a methylsulphinyl group and/or wherein C' is a hydroxy or a methylsulphinyl group and C is a hydrogen have from 1 to 3 asymetric centers. They may therefore exist in the form of various diastereo-isomers which may be isolated by means of chemical, physical or enzymatic methods. The resulting diastereo-isomeric forms may be further be resolved into their optical isomers.

The diastereo-isomeric forms and the optical isomers thereof are part of this invention.

Depending on the meanings of the various substituents three distinct subgroups, equally interesting, may be evidenced:

(1) The 4-naphtoyl derivatives having the general formula $I_A$:

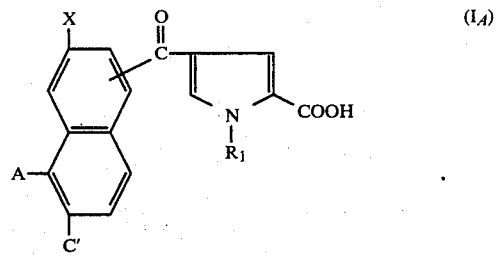

wherein:
X is a methylsulphinyl group and C' is a hydrogen; or
X is a hydrogen and C' is a methylsulphinyl group;
A is a hydrogen or a hydroxy; and
$R_1$ has the previously-given meanings.

(2) The dihydronaphthalene diols of the general formula $I_B$:

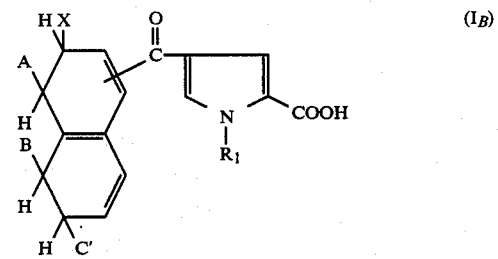

wherein:
X is a hydroxy and A is a hydroxy;
B and C' are both a hydrogen; or B and C' are both a hydroxy and X and A are both a hydrogen; and
$R_1$ has the above-given definitions.

(3) The desalkylated derivatives of the general formula $I_C$:

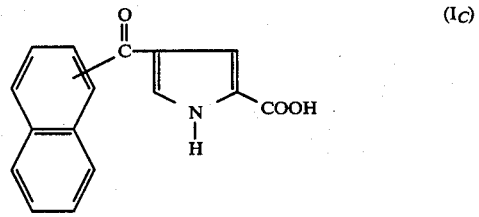

wherein the naphthyl ring may further include a hydroxy or a methylsulphinyl substituent.

In each of these structures the naphthyl ring is bound to the carbonyl through the carbon-1 or the carbon-2.

The compounds of formula I and their base addition salts with a mineral or organic base are endowed with interesting pharmacological properties. They more particularly show immunological properties and precisely immuno-suppressive properties. Moreover some compounds and namely the (3-methylsulfonylnaphthoyl-1) derivative and the (3-hydroxy or 5-hydroxynaphthoyl-1)-pyrrolyl-2-carboxylic acids show depending on the doses either immuno-suppressive or immuno-stimulating properties.

Due to their low toxicity, they may found a use in human or veterinary therapy and more particularly as a medicine for the immunological disturbances.

As immuno-suppressive drugs they found a use in human or veterinary medicine as a treatment of auto-immune diseases such as erythematons lupus, rheumatoidal polyarthritis, insulino-dependant diabetes of the young, myopathias, and some renal diseases. They also are suitable for preventing or avoiding the phenomena of rejection after implantation of grafts or graft of tissues.

As an immuno-stimulating drug they found a use in human or veterinary medicine for the treatment of chronic diseases such as bronchitis or for the increase of phenomena of healing of the wounds.

For these purposes they are dispensed in the form of pharmaceutical compositions having as active ingredient at least a compound of general formula I or a mineral or organic base addition salt in conjunction or admixture with an inert non-toxic pharmaceutically-compatible vehicle or carrier.

The excipient or the vehicle are one of those suitable for administration through parenteral, digestive, rectal or topic routes of administration. It may be particularly cited the aqueous or saline solutions, the starches, the celluloses, the alkylcelluloses, carboxymethylcelluloses, carboxymethyl starches, earth alkaline metal phosphates or carbonates, magnesium phosphate, cacao butter or polyethyleneglycol stearates.

The pharmaceutical compositions according to this invention are manufactured in the form of uncoated or coated tablets, dragees, pills, capsules, soft capsules, drinkable solutions or suspensions, injectible solutions divided into ampuls, multidoses flasks, or auto-injectible syringes, suppositories, rectal capsules, creams or pressurized sprays for percumous applications.

The efficient dosology may vary within a broad range depending of the way of administration, the weight or age of the patient and on the therapeutic aim. As a general rule the unit dosology ranges from 25 to 1 500 mg per unit dosage and the daily dosage range from 25 to 2 000 mg in the adult.

The pharmaceutical compositions according to this invention are prepared on an industrial scale according to the methods conventionally utilized in the pharmacotechny.

The compounds of general formula I and the base addition salts thereof are prepared by the known methods of the organic chemistry starting from aroylpyrrolyl-2-carboxylic acids of the general formula II:

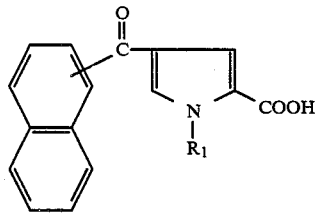

(II)

previously described in the French Pat. No. 2,405,246.

They may also be isolated in the biological fluids and particularly from the urine after administration of the said aroylpyrrolyl-2-carboxylic acids to animals and extraction using the usual physical methods.

The compounds of formula I after purification are defined by means of the most performing analytical date such as mass spectra.

BRIEF DESCRIPTION OF THE DRAWINGS

The mass spectra of certain compounds within the scope of the present invention are illustrated in the figures as follows:

FIG. I shows the mass spectra of:
a. N-methyl-4-(naphthoyl-1)-pyrrolyl-2-carboxylic acid.
b. N-(naphthoyl-1)-pyrrolyl-2-carboxylic acid by synthesis.
c. 4-(naphthoyl-1)-pyrrolyl-2-carboxylic acid obtained by biological extraction.

Figure 1A:
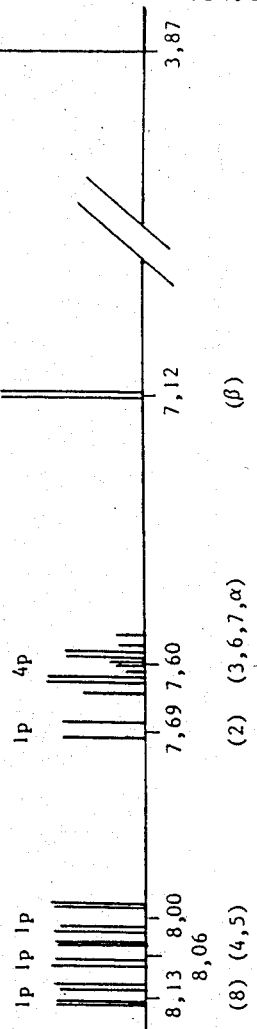
Figure 1B:
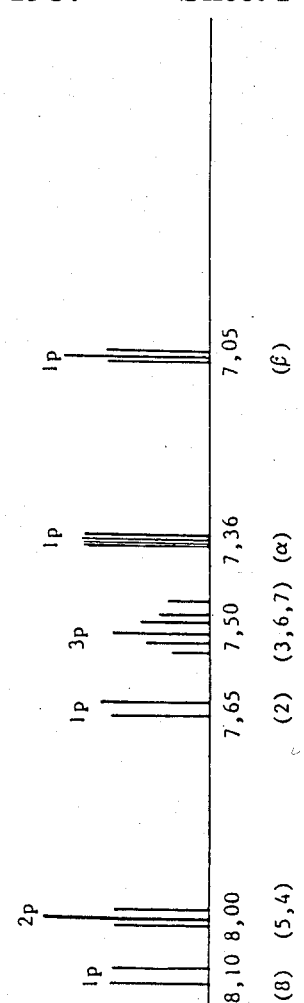
Figure 1C:
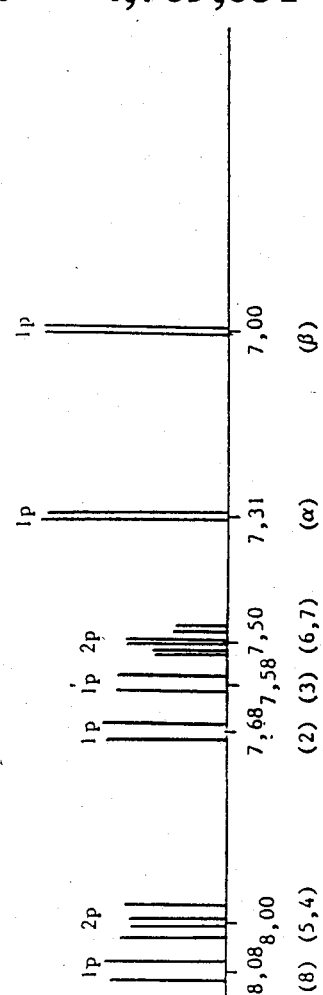
Figure 2A:
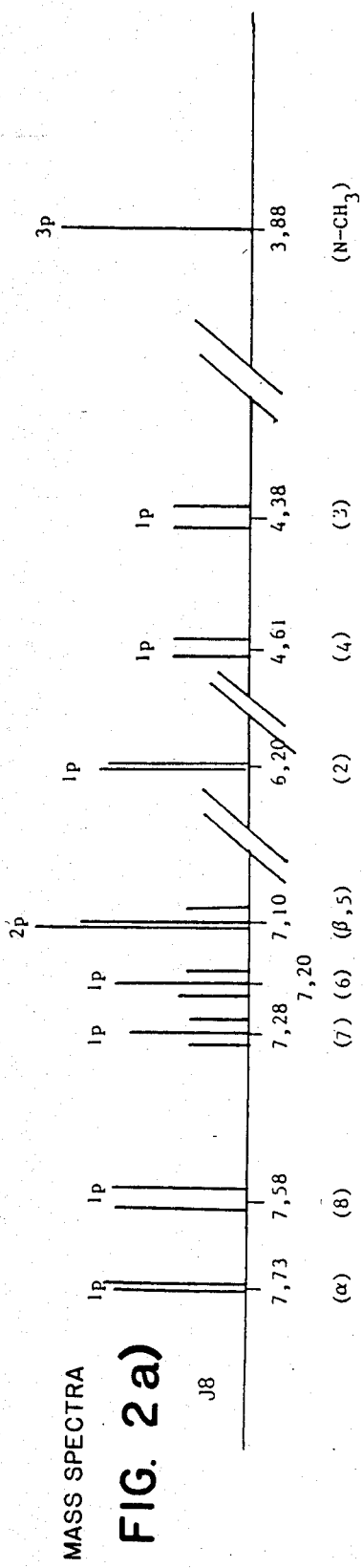
Figure 2B:
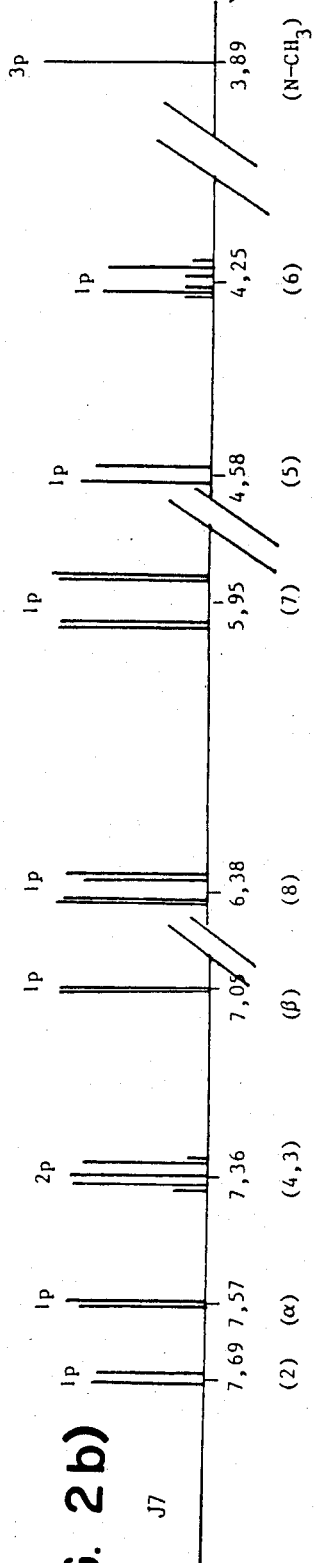
Figure 3A:
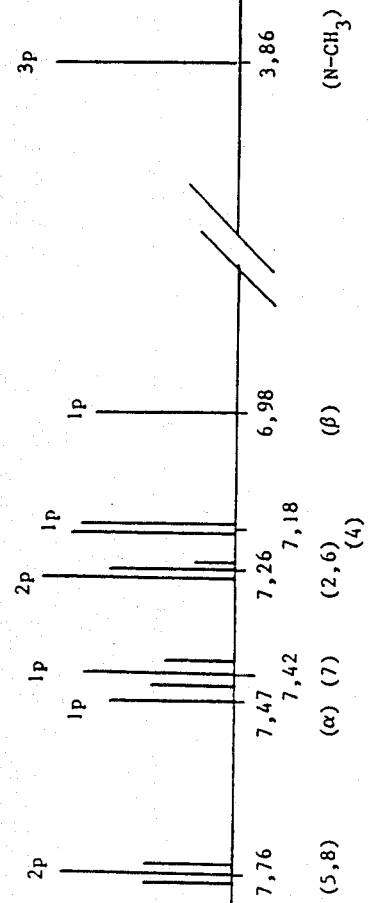
Figure 3B:
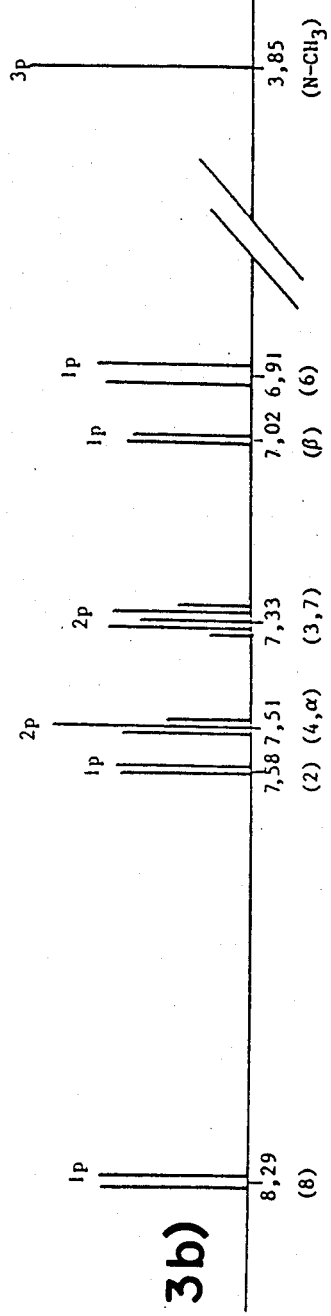
Figure 5:
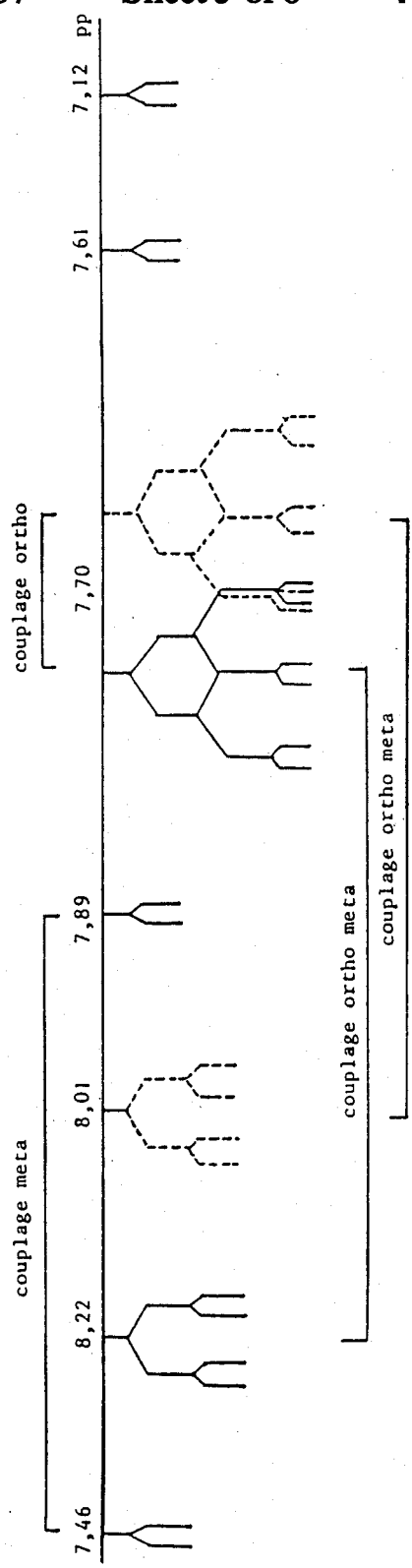
Figure 6:
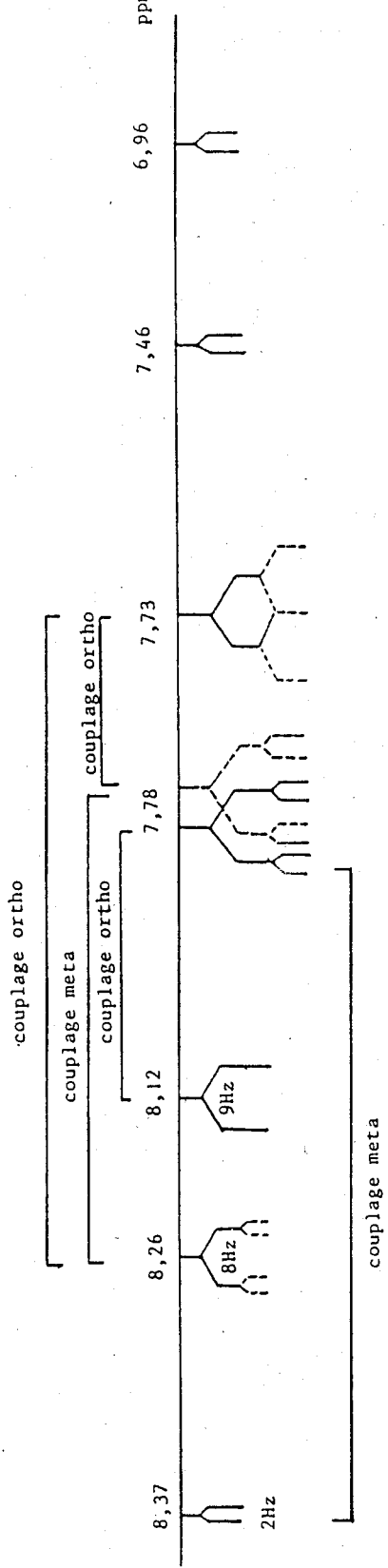

FIG. II shows the mass spectra of:
a. N-methyl-(5,6-dihydroxy-5,6-dihydronaphthoyl-1)pyrrolyl-2-carboxylic acid
b. N-methyl-(3.4-dihydroxy-3.4-dihydronaphthoyl-1pyrrolyl-2-carboxylic acid.

FIG. III shows the mass spectra of:
a. N-methyl-4-(3-hydroxy-naphthoyl-1)-pyrrolyl-2-carboxylic acid obtained by extraction.
b. N-methyl-4-(5-hydroxynaphthoyl-1)-pyrrolyl-2-carboxylic acid recovered by extraction.

FIG. IV shows the mass spectra of:
a. N-methyl-4-(3-methylsulphinylnaphthoyl-1)-pyrrolyl-2-carboxylic acid.
b. N-methyl-4-(6-methylsulphinylnaphthoyl-1)-pyrrolyl-2-carboxylic acid.

FIG. V shows the coupling after successive irradiations at (8.46), (8.22), (8.01) ppm and interpretation of the aromatic moiety of the NMR spectrum of the (3-methylsulphinylnaphthoyl-1) derivative recovered by HPLC.

FIG. IV shows the coupling after successive irradiations at (8.46), (8.22), and (8.01) ppm and signification of the aromatic moiety of the RMN spectrum of N-methyl-4-(6-methylsulphinylnaphthoyl-1)-pyrrolyl-2-carboxylic acid.

The following examples are merely intended to illustrate the invention. They do not limit it in any manner.

EXAMPLE I

TABLE I

MAIN PEAKS OBTAINED FROM MASS SPECTRA OF N—METHYL-4(NAPHTHOYL-1)-PYRROLYL-2-CARBOXYLIC ACID TAKEN AS REFERENCE COMPOUND

| Electronic Impact WEIGHT | percentage | |
|---|---|---|
| 279 | 18 | ⟶ molecular peak |
| 262 | 80 | ⟶ loss of OH or $H_2O$ (−17) |
| 234 | 80 | ⟶ loss of COOH |
| 218 | 10 | |
| 205 | 10 | |
| 190 | 10 | |
| 165 | 20 | |
| 152 | 100 | ⟶ 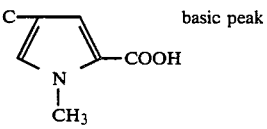 basic peak |
| 134 | 12 | |
| 127 | 60 | ⟶ naphthyl$^+$ |
| 108 | 10 | ⟶ 152 (−$CO_2$) |
| 58 | 90 | |

TABLE II

MEAN PEAKS OBTAINED FROM THE MASS SPECTRA OF THE N—DEMETHYL DERIVATIVE OBTAINED AFTER EXTRACTION

| Electronic Impact | | Chemical Ionization | |
|---|---|---|---|
| \multicolumn{4}{c}{4-(naphthoyl-1)-pyrrolyl-2-carboxylic acid} | | | |
| 265 | 64% - molecular peak | 282 | 19% - molecular ion + $NH_4^+$ |
| 246 | 22% - loss of water (−19) | 279 | 11% |
| 230 | 5% - (−35) | 266 | 100% - molecular ion + $H^+$ |
| 220 | 64% - loss of COOH | 157 | |
| 204 | 4% | | |
| 190 | 18% | | |
| 165 | 15% | | |
| 155 | 7% - [naphthyl−C≡O$^+$] | | |
| 138 | 21% - [O≡C−pyrrolyl−COOH] | | |
| 127 | 46% | | |
| 120 | 100% | | |

After treatment with Diazomethane

| | | | |
|---|---|---|---|
| 279 | 25% - molecular peak | 297 | 10% - molecular ion + $NH_4^+$ |
| 246 | 8% (−33) | 294 | 18% - contamination of the previous one |
| 234 | 5% | | |
| 220 | 31% | 280 | 100% - molecular ion + $H^+$ |
| 190 | 10% | | |
| 175 | 8% | | |
| 166 | 8% | | |
| 155 | 13% | | |
| 153 | 20% | | |
| 144 | 19% | | |
| 127 | 39% | | |
| 120 | 57% | | |
| 100 | 100% | | |

TABLE III

MEAN PEAKS OBTAINED FROM THE MASS SPECTRA OF SYNTHETIC N—DEMETHYL DERIVATIVE 4-(naphthoyl-1)-pyrrolyl-2-carboxylic acid

| Electronic Impact | | Chemical Ionization $NH_3$ | |
|---|---|---|---|
| 265 | 57% molecular peak | 266 | 100% molecular ion + $H^+$ |
| 246 | 23% loss of water (−19) | 246 | 7% loss of water |
| 230 | 7% (−35) | 220 | 28% loss of COOH |
| 220 | 75% loss of COOH | | |
| 204 | 5% | | |
| 190 | 16% | | |
| 165 | 6% | | |
| 155 | 3% [naphthyl−C≡O] | | |
| 138 | 8% [O≡C−pyrrolyl−COOH] | | |

TABLE III-continued

MEAN PEAKS OBTAINED FROM THE MASS SPECTRA OF SYNTHETIC N—DEMETHYL DERIVATIVE
4-(naphthoyl-1)-pyrrolyl-2-carboxylic acid

| Electronic Impact | | Chemical Ionization NH3 |
|---|---|---|
| 127 | 24% naphthalene | |
| 120 | 100% | |
| 95 | 28% | |
| 69 | 90% | |

After treatment with Diazomethane formation of the methylester ⟵  280  100% molecular ion + H$^+$ 246  5%
220  22%

EXAMPLE II

Preparation and identification of N-methyl-4-(5.6-dihydroxy-5.6-dihydronaphthoyl-1)-pyrrolyl-2-carboxylic acid.

EXAMPLE III

N-methyl-4-(3.4-dihydroxy-3.4-dihydronaphthoyl-1)-pyrrolyl-2-carboxylic acid.

TABLE IV

MAIN PEAKS OBTAINED FROM THE MASS SPECTRA OF THE (5.6-DIHYDROXY-5.6-DIHYDRONAPHTHOYL-1) DERIVATIVE
i.e.
N—methyl-4-(5.6-dihydroxy-5.6-dihydronaphthoyl-1)pyrrolyl-2-carboxylic acid

| Electronic Impact | | Chemical ionization NH3 | | |
|---|---|---|---|---|
| 313 | 10% molecular peak | 331 | 6% | molecular ion + NH$_4^+$ |
| 295 | 6% loss of water | 314 | 100% | molecular ion + H$^+$ |
| 285 | 5% loss of −28 ? | 296 | 6% | loss of water |
| 269 | 12% loss of COOH | 280 | 4% | loss of oxygen (?) |
| 250 | 6% loss of COOH + H$_2$O | 270 | 8% | loss of COOH |
| 251 | | 214 | 15% | |
| 240 | 3% | 154 | 7% | |
| 222 | 6% | | | |
| 206 | 2% | | | |
| 184 | 25% | | | |
| 152 | 30% | O≡C—[pyrrole ring with COOH, N-CH$_3$] | | |
| 115 | 30% | | | |
| 115 | 30% | | | |
| 108 | 40% | | | |
| 58 | 100% basic peak | | | |

After treatment with Diazomethane

| 327 | 65% Acid + CH$_3$ = Methylester |
| 309 | 5% loss of water |
| 299 | 30% |
| 283 | 22% |
| 250 | 20% |
| 240 | 30% |
| 166 | 100% basic peak |

TABLE V

MAIN PEAKS OBTAINED FROM THE MASS SPECTRA OF THE N—METHYL-4-(3.4-DIHYDROXY-3.4-DIHYDRONAPHTHOYL-1 PYRROLYL-2-CARBOXYLIC DERIVATIVE

| Electronic Impact | | | Chemical Ionization NH3 | | |
|---|---|---|---|---|---|
| 313 | 15% | molecular peak | 314 | 32% | molecular ion + H |
| 295 | 12% | loss of water | 296 | 65% | loss of water |
| 279 | 5% | loss of −34 | 280 | 8% | |
| 269 | 7% | loss of COOH | 270 | 24% | |
| 250 | 5% | | 252 | 100% | basic peak |

TABLE V-continued

MAIN PEAKS OBTAINED FROM THE MASS SPECTRA OF THE N—METHYL-4-(3.4-DIHYDROXY-3.4-DIHYDRONAPHTHOYL-1 PYRROLYL-2-CARBOXYLIC DERIVATIVE

| Electronic Impact | | Chemical Ionization NH₃ | |
|---|---|---|---|
| 234 | 8% | 152 | 19% |
| 222 | 5% | | |
| 206 | 2% | | |
| 194 | 8% | | |
| 170 | 2% | | |
| 152 | 100% | | |
| 134 | 8% | | |
| 131 | 15% | | |
| 115 | 30% | | |
| 108 | 70% | | |
| 103 | 20% | | |
| 58 | 40% | | |
| After treatment with Diazomethane | | | |
| 327 | 14% | Acid + CH₃=Methylester | |
| 309 | 16% | loss of water | |
| 250 | 16% | | |
| 166 | 100% | | |
| 152 | 10% | | |

EXAMPLE IV

N-methyl-4-(3-hydroxy-naphthoyl-1)-pyrrolyl-2-carboxylic acid and N-methyl-4-(5-hydroxynaphthoyl-1)-pyrrolyl-2-carboxylic acid.

TABLE VI

MAIN PEAKS OBTAINED FROM THE MASS SPECTRA FROM N—METHYL-4-(3-HYDROXYNAPHTHOYL-1)-PYRROLYL-2-CARBOXYLIC ACID OBTAINED BY EXTRACTION

| Electronic Impact | | Chemical Ionization | |
|---|---|---|---|
| No mass higher than 100 | | 296 | 100%-molecular ion + H⁺ |
| | | 252 | 60%-loss of COOH |
| After treatment with Diazomethane | | | |
| 323 | 54%-dimethylated derivative | 324 | 100%-dimethylated derivative + H⁺ |
| 306 | 6%-loss of 17 | | |
| 292 | 6%-loss of OCH₃ | | |
| 264 | 63%-loss of COOCH₃ | | |
| 195 | 4% | | |
| 185 | 8% | | |
| 166 | 100% | | |
| 134 | 31% | | |
| 114 | 20% | | |
| 99 | 53% | | |

TABLE VII

MAIN PEAKS OBTAINED FROM THE MASS SPECTRA OF N—METHYL-4-(5-HYDROXYNAPHTHOYL-1)-PYRROLYL-2-CARBOXYLIC ACID RECOVERED BY EXTRACTION

| Electronic Impact | | Chemical Ionization | |
|---|---|---|---|
| 295 | 1,9%-molecular peak | | |
| 281 | 0,4%-loss of CH₃ | | |
| 279 | 1,2%-loss of oxygen | | |
| 278 | 0,6%-loss of water | | |

TABLE VII-continued

MAIN PEAKS OBTAINED FROM THE MASS SPECTRA OF N—METHYL-4-(5-HYDROXYNAPHTHOYL-1)-PYRROLYL-2-CARBOXYLIC ACID RECOVERED BY EXTRACTION

| Electronic Impact | | Chemical Ionization | |
|---|---|---|---|
| 250 | 2,2%-loss of COOH | | |
| 234 | 0,8%-(compound 250 loss of oxygen) | | |
| 220 | 2,0% | | |
| 211 | 4,0% | | |
| 180 | 1,2% | | |
| 172 | 3,4% | | |
| 166 | 1,9% | | |
| 152 | 4,0% | | |
| 122 | 21% | | |
| 105 | 31% | | |
| 99 | 30% | | |
| 91 | 23% | | |
| 86 | 24% | | |
| 84 | 46% | | |
| 77 | 26% | | |
| 58 | 100% | | |
| After treatment with Diazomethane | | | |
| 23 | 16%-dimethylated derivative | 324 | 98%-dimethylated derivative + H⁺ |
| 309 | 48%-monomethylated derivative | 310 | 100%-monomethylated derivative + H⁺ |
| 292 | 16% | 280 | 30%  ? |
| 264 | 12% | | |
| 250 | 50% | | |
| 180 | 21% | | |
| 166 | 100% | | |

EXAMPLE V

N-methyl-4-(3-methylsulphinylnaphthoyl-1)-pyrrolyl-2-carboxylic acid and N-methyl-4-(6-methylsulphinylnaphthoyl-1)-pyrrolyl-2-carboxylic acid.

TABLE VIII

MAIN PEAKS OBTAINED FROM THE MASS SPECTRA OF
N—METHYL-4-(3-METHYLSULPHINYLNAPHTHOYL-1)-PYRROLYL-2-CARBOXYLIC
ACID RECOVERED AFTER EXTRACTION BY HPLC

| Electronic Impact | | | Chemical Ionization $NH_3$ | | |
|---|---|---|---|---|---|
| 341 | 10% | molecular peak | 359 | 15% | molecular ion + $NH_4^+$ |
| 325 | 41% | loss of oxygen | 342 | 100% | molecular ion + $H^+$ |
| 297 | 7% | loss of COOH | 326 | 30% | loss of oxygen |
| 281 | 38% | | 298 | 10% | loss of COOH |
| 211 | 11% | | 282 | 10% | (298 - oxygen) |
| 205 | 7% | | 267 | 4% | (298 - methoxy) |
| 167 | 26% | | 236 | 3% | |
| 152 | 100% | [structure: O≡C-pyrrole-COOH with N-CH3] | 223 | 4% | |
| | | | 205 | 2% | |
| | | | 191 | 6% | (naphthalene 30 $SOCH_3$) |
| | | | 152 | 6% | |
| 129 | 34% | | | | |
| 108 | 79% | | | | |
| 91 | 36% | | | | |
| | | After treatment with Diazomethane | | | |
| 355 | 12% | molecular peak | 356 | 100% | molecular ion + $H^+$ |
| 340 | 12% | loss of $CH_3$ | 342 | 70% | loss of $CH_3$ |
| 324 | 1% | loss of oxygen and $CH_3$ | 340 | 80% | loss of oxygen |
| 308 | 1% | | 326 | 20% | loss of oxygen and $CH_3$ |
| 296 | 1% | (peak 340 - COOH) | 324 | 10% | loss of two oxygens |
| 282 | 1% | | 298 | 10% | |
| 223 | 2% | | 294 | 15% | (loss of $SOCH_3$ ?) |
| 166 | 30% | | 282 | 8% | |
| 163 | 2% | | 191 | 6% | |
| 113 | 40% | | 155 | 20% | |
| 104 | 25% | | | | |
| 83 | 30% | | | | |
| 59 | 100% | | | | |

TABLE IX

MAIN PEAKS OBTAINED FROM THE MASS SPECTRA OF
(6-METHYLSULPHINYLNAPHTHOYL-1)-N—METHYL-PYRROLYL-2-CARBOXYLIC ACID

| Electronic Impact | | | Chemical Ionization | | |
|---|---|---|---|---|---|
| 341 | 7% | molecular peak | 359 | 2% | molecular ions + $NH_4^+$ |
| 325 | 12% | loss of an oxygen | 342 | 100% | molecular ion + $H^+$ |
| 281 | 16% | (peak 325 - loss of COOH) | 326 | 7% | (loss of $CH_3$) |
| 267 | 5% | (peak 281 - loss of $CH_3$) | 298 | 6% | (loss of COOH) |
| 152 | 95% | [structure: O≡C-pyrrole-COOH with N] | 282 | 6% | (peak 298 - loss of an oxygen) |
| 129 | 50% | | 267 | 12% | (peak 298 - loss of $OCH_3$) |
| 108 | 41% | | 223 | 6% | |
| 105 | 100% | | 205 | 2% | |
| | | | 191 | 5% | (naphthalene - $SOCH_3$ ?) |
| | | | 152 | 3% | |
| | | After treatment with Diazomethane | | | |
| 355 | 2% | molecular peak | 373 | 7% | molecular ion + $NH_4^+$ |
| 340 | 3% | (loss of $CH_3$) | 356 | 100% | molecular ion + $H^+$ |
| 162 | 1% | | 340 | 35% | (loss of an oxygen) |
| 132 | 8% | | 294 | 3% | (loss of two oxygens) |
| 113 | 20% | | 282 | 3% | (loss of $SOCH_3$ ?) |
| 83 | 15% | | 261 | 2% | |
| 71 | 100% | | 167 | 1% | |
| 70 | 95% | | 155 | 6% | |

EXAMPLE VI

Study of the compounds of this invention as immuno-suppressive agents

Azathioprin and N-methyl-4-(naphthoyl-1)-pyrrolyl-2-carboxylic acid have been selected as reference products.

(A) Action of the compounds according to this invention "in vitro" in the test of Rosettes This study has been carried out on blood red cells of sheep contacted with spleen cells of mice of the strain $C_{57}BL/6J$. The modulation of the appearance of rosettes by the compounds according to this invention in comparison with that produced by Azathioprin, has given the following results.

1. Azathioprin inhibits the formation of rosettes at concentrations ranging from 1 to 10 μg/ml.
2. N-methyl-4-(naphthoyl-1)-pyrrolyl-2-carboxylic acid inhibits the formation of rosettes in about the same percentages at concentrations also ranging from 1 to 10 μg/ml.
3. 4-(naphthoyl-1)-pyrrolyl-2-carboxylic acid has an inhibition action of about the same order than that of the N-methylated derivative.
4. N-methyl-4-(5-hydroxylnaphthoyl-1)pyrrolyl-2-carboxylic acid is also an inhibitor to a similar degree and further possesses an immuno-stimulating activity of low doses.
5. N-methyl-4-(5.6-dihydroxy-5.6-dihydronaphthoyl-1)-pyrrolyl-2-carboxylic acid and N-methyl-4-(3-methylsulphinylnaphthoyl-1)-pyrrolyl-2-carboxylic acid have an inhibitory action similar to that of N-methyl-4-(naphthoyl-1)-pyrrolyl-2-carboxylic acid.
6. N-methyl-4-(3-hydroxynaphthoyl-1)-pyrrolyl-2-carboxylic acid has a mixed immuno-stimulating activity at concentrations ranging from 1 to 10 μg/ml.

Conclusively the derivatives of N-methyl-4-(naphthoyl-1)-pyrrolyl-2-carboxylic acid in nitro modulates the formation of rosettes at nearly the effective concentrations of Azathioprin. The N-methyl-4-(3-hydroxynaphthoyl-1)-pyrrolyl-2-carboxylic derivative further shows the particular property to stimulate the formation of rosettes.

(B) Study of the activity of the compounds according to this invention in the test of lymphoblastic conversion In the test of lymphoblastic conversion these compounds show an antimitotic activity at doses ranging from 5 to 50 μg/ml. For some compounds such as the 3-methylsulphinyl- and the N-demethyl derivative, it may be noticed a stimulating activity at low doses as well as opposite Concanavalin A as opposite LPS (Lipopolysaccharids of Escherichia Coli). The evidencing of an immuno-stimulating activity for some of the compounds according to this invention may open the way to another therapeutic field.

What we claim is:
1. The naphthoyl derivatives of pyrrolyl-carboxylic acid selected from the group consisting of:
(a) an acid derivative of the formula

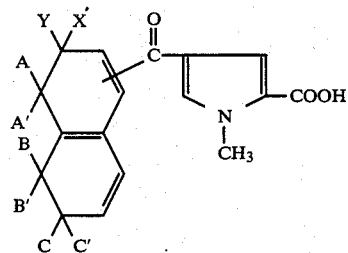

(I)

wherein:
X is hydrogen, hydroxy or methylsulphinyl
Y is hydrogen, or together with A' forms a double bond;
A is hydrogen, or hydroxy;
A' is hydrogen or together with Y forms a double bond;
B is hydrogen or hydroxy;
B' is hydrogen or together with C forms a double bond;
C is hydrogen, or together with B' forms a double bond;
C' is hydrogen, hydroxy or methylsulphinyl with the proviso that at least one member of the group X, A, B, and
C' is other than hydrogen and one member only of the group X, and C' is methylsulfinyl or hydroxy; and
(b) the base addition of salts thereof with a therapeutically compatible mineral or organic base.

2. A compound according to claim 1 having the formula $1_A$:

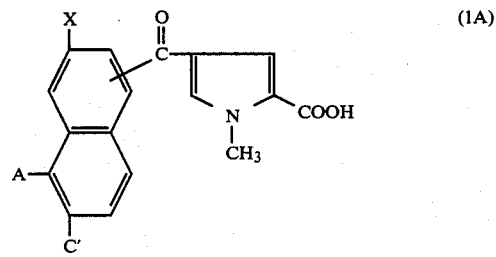

(1A)

wherein
X is methylsulphinyl group and C' is hydrogen;
or X is hydrogen and C' is methylsulphinyl and
A is hydrogen or hydroxy.

3. A compound according to claim 1 selected from the group consisting of:
(a) 5-6 dihydrodiols of the formula

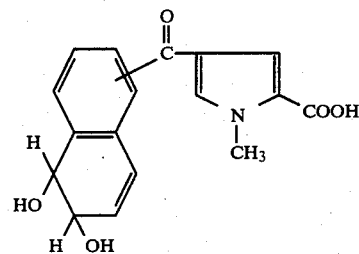

(b) and the 3,4 dihydrodiols of the formula

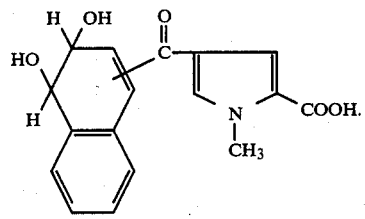

4. A compound according to claim 1 namely N-methyl-4-(3,4-dihydroxy-3,4,-dihydronaphthoyl-1)-pyrrolyl-2-carboxylic acid.
5. A compound according to claim 1 namely N-methyl-4-(5,6-dihydroxy-5,6-dihydronaphthoyl-1)-pyrrolyl-2-carboxylic acid.
6. A compound of claim 1 namely N-methyl-4-(6-methylsulfinyl naphtholyl-1)-pyrrolyl-2-carboxylic acid.
7. A compound of claim 1 namely N-methyl-4-(3-methylsulfinyl naphtholyl-1)-pyrrolyl-2-carboxylic acid.

* * * * *